United States Patent
Kawachi (10) Patent No.: US 9,610,008 B2
(45) Date of Patent: Apr. 4, 2017

(54) ENDOSCOPE REPROCESSOR (71) Applicant: OLYMPUS CORPORATION, Tokyo (JP)

(72) Inventor: Shinichiro Kawachi, Inagi (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/141,959

(22) Filed: Apr. 29, 2016

(65) Prior Publication Data

US 2016/0242636 A1  Aug. 25, 2016

Related U.S. Application Data

(63) Continuation of application No. PCT/JP2015/062841, filed on Apr. 28, 2015.

(30) Foreign Application Priority Data

Aug. 21, 2014 (JP) ................. 2014-168621

(51) Int. Cl.
*A61B 1/12* (2006.01)
*B08B 3/04* (2006.01)

(52) U.S. Cl.
CPC ............. *A61B 1/123* (2013.01); *A61B 1/12* (2013.01); *A61B 1/125* (2013.01); *B08B 3/04* (2013.01)

(58) Field of Classification Search
None
See application file for complete search history.

(56) References Cited

U.S. PATENT DOCUMENTS

2007/0154343 A1* 7/2007 Kral .................. A61B 1/125
  422/1
2014/0134071 A1* 5/2014 Suzuki .................. A61L 2/18
  422/296

FOREIGN PATENT DOCUMENTS

| EP | 2803314 A1 | 11/2014 |
| JP | H04-38925 A | 2/1992 |
| JP | H04-312440 A | 11/1992 |
| JP | 2008-142420 A | 6/2008 |

(Continued)

OTHER PUBLICATIONS

Japanese Office Action dated Nov. 4, 2015 issued in JP 2015-542895.

(Continued)

*Primary Examiner* — Michael Barr
*Assistant Examiner* — Cristi Tate-Sims
(74) *Attorney, Agent, or Firm* — Scully, Scott, Murphy & Presser, P.C.

(57) ABSTRACT

An endoscope reprocessor includes: a processing tank including a first tank that is arranged at a lowermost tier, and a second tank that communicates with the first tank, the processing tank allowing an endoscope to be placed in the processing tank; a drainage port arranged in the first tank; a first water level detection section that detects whether or not a first water level set to be a water level that is equal to or below a boundary between the first tank and the second tank is submerged in water; a circulation port that opens at a level that is below the first water level; a circulation conduit including one end connected to the circulation port and another end that opens at a position that is above the first water level in the processing tank; and a circulation pump that is provided in the circulation conduit.

6 Claims, 9 Drawing Sheets

(56) References Cited

FOREIGN PATENT DOCUMENTS

WO    2014/045718 A1    3/2014

OTHER PUBLICATIONS

International Search Report dated Aug. 4, 2015 issued in PCT/JP2015/062841.

* cited by examiner

ENDOSCOPE REPROCESSOR

CROSS REFERENCE TO RELATED APPLICATION

This application is a continuation application of PCT/JP2015/062841 filed on Apr. 28, 2015 and claims benefit of Japanese Application No. 2014-168621 filed in Japan on Aug. 21, 2014, the entire contents of which are incorporated herein by this reference.

BACKGROUND OF THE INVENTION

1. Field of the Invention

The present invention relates to an endoscope reprocessor that subjects an endoscope to processing using a liquid.

2. Description of the Related Art

Endoscopes used in a medical field are subjected to cleaning processing and disinfecting processing after use. An endoscope cleaning/disinfecting processing apparatus that automatically performs cleaning processing and disinfecting processing of an endoscope is disclosed in, for example, Japanese Patent Application Laid-Open Publication No. 2008-142420.

An endoscope cleaning/disinfecting apparatus includes a processing tank that allows an endoscope to be placed inside, and in the processing tank, a liquid such as water, a cleaning liquid or a disinfecting liquid is stored, and an endoscope is immersed in the liquid to perform rinsing processing, cleaning processing or disinfecting processing.

After use, the liquid stored in the processing tank is discharged to the outside of the endoscope cleaning/disinfecting apparatus via a drainage port provided in a bottom face portion of the processing tank and a discharge conduit connected to the drainage port. A hose arranged outside the apparatus is connected to the discharge conduit. In a drainage process of discharging a liquid in a processing tank in a conventional endoscope cleaning/disinfecting apparatus, timer control in which the discharge is performed for a predetermined period of time and the liquid in the processing lank is thereby regarded as being completely discharged is performed. The timer control requires a time period of waiting until the liquid in the processing tank is discharged in the drainage process to be set to be longer than at maximum value of a time period actually required for the discharge, and thus causes a wasted waiting time period.

Therefore, for example, in a dish washer disclosed in Japanese Patent Application Laid-Open Publication No. 4-38925, a water level sensor is provided at a position of a predetermined level in a processing tank that subjects dishes to washing processing, and at the time of a drainage process, a time period of lowering of a liquid surface in the processing tank from the start of drainage to a position of the water level sensor is measured, and based on the time period, a time period required for discharge of the remaining liquid is determined and a wasted wait time period is thereby reduced.

SUMMARY OF THE INVENTION

An endoscope reprocessor according to an aspect of the present invention includes: a processing tank including a first tank that has a predetermined capacity and is arranged at a lowermost tier, and a second tank that communicates with the first tank, the processing tank allowing an endoscope to be placed in the processing tank; a drainage port arranged in the first tank; a restriction portion that restricts the endoscope from entering the first tank; a first water level detection section that detects whether or not as first water level set to be a water level that is equal to or below a boundary between the first tank and the second tank is submerged in water; a circulation port that opens at a level that is below the first water level and is a predetermined distance above a bottom face of the first tank in the processing tank; a circulation conduit including one end connected to the circulation port and another end that opens at a position that is above the first water level in the processing tank; and a circulation pump that transfers a fluid in the circulation conduit from the one end toward the other end.

DETAILED DESCRIPTION OF THE PREFERRED EMBODIMENTS

Preferred embodiments of the present invention will be described with reference to the drawings. Note that in each of the drawings used for the following description, components are illustrated on difference scales so that the respective components have sizes that are large enough to be recognized in the drawing, and the present invention is not limited only to the counts and amounts, and the shapes of the components, and the size ratios and the relative positional relationships among the respective components illustrated in the drawings.

First Embodiment

A first embodiment, which is an example of an embodiment of the present invention, will be described below. An endoscope reprocessor 1 is an apparatus that performs reprocessing of an endoscope 100 or an endoscope accessory. Reprocessing mentioned here is not specifically limited, and may be water rinsing, cleaning for removing dirt of, e.g., organic substances, disinfection for making predetermined microorganisms harmless and sterilization for eliminating or killing all microorganisms or any combination thereof.

Figure 1:
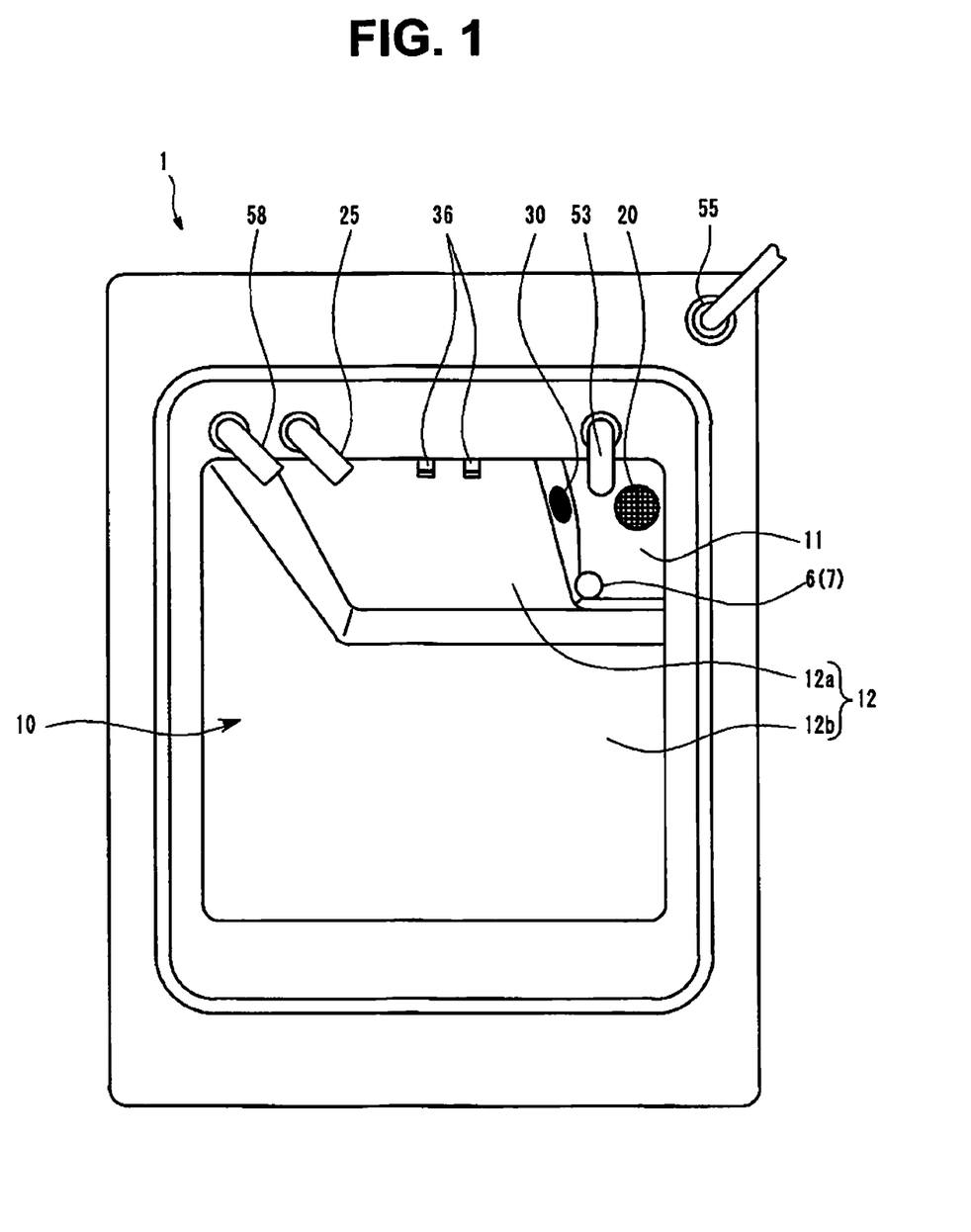
FIG. 1 is a view of a processing tank in an endoscope reprocessor according to a first embodiment as viewed from above.
Figure 2:
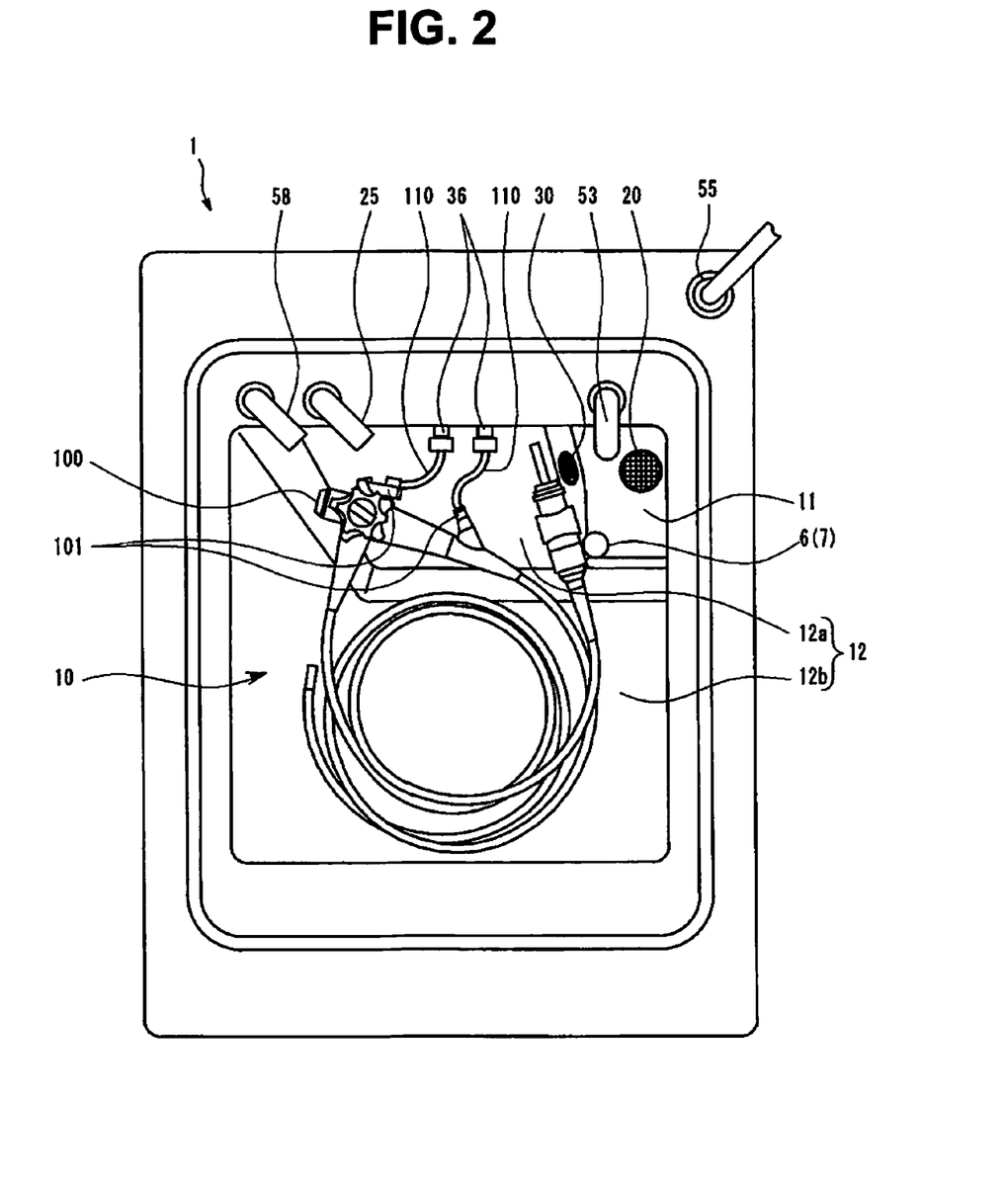
FIG. 2 is a diagram of a state in which an endoscope is placed in the processing tank in the endoscope reprocessor according to the first embodiment.
Figure 3:
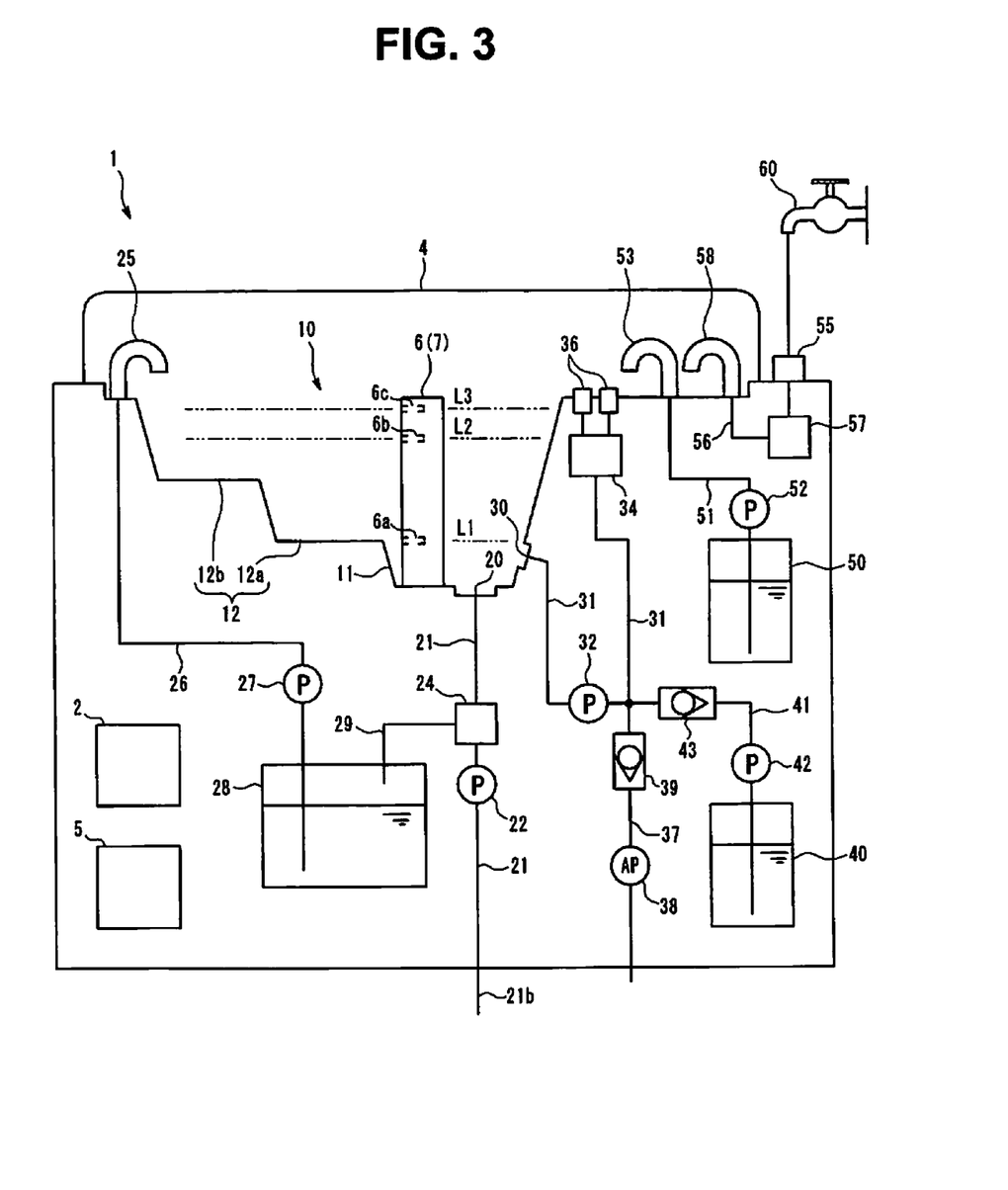
FIG. 3 is a diagram illustrating a configuration of the endoscope reprocessor according to the first embodiment.

Note that in the following description, "down", "lower" and "below" indicate a direction of gravitational force and "up", "upper" and "above" indicate a direction opposite to the direction of gravitational force. FIG. 1 is a top-down view of a processing tank 10 in the endoscope reprocessor 1. FIG. 2 is a diagram illustrating a state in which an endoscope 100 is placed in the processing tank 10. FIG. 3 is a diagram illustrating a schematic configuration of the endoscope reprocessor 1.

As illustrated in FIG. 3, the endoscope reprocessor 1 includes a control section 2, a power supply apparatus 5, the processing tank 10 that allows an endoscope 100 to be placed therein, a restriction portion 7 and a water level sensor 6.

The control section 2 is an apparatus that controls operation of each of later-described components of the endoscope reprocessor 1, based on a predetermined program, and includes, for example, a computer including, e.g., an arithmetic operation apparatus, a storage apparatus, an auxiliary storage apparatus and an input/output apparatus. Also, the control section 2 may include a timing section that measures passage of time.

The power supply apparatus 5 supplies power to the control section 2 and other components of the endoscope reprocessor 1. The power supply apparatus 5 may be configured so as to receive power from a commercial power supply and supply the power to the respective components, or may include a primary battery, a secondary battery or a power generation apparatus to supply power to the respective components.

The processing tank 10 has a recessed shape including an opening portion that opens upward, and enables an endoscope 100 to be placed inside. The processing tank 10 enables a liquid to be stored inside, and also enables a liquid existing inside to be discharged from a later-described drainage port 20 to the outside.

Note that although the illustration is omitted in FIG. 1, as illustrated in FIG. 3, a lid 4 for opening/closing the opening portion is provided at the processing tank 10. Where processing of an endoscope 100 is performed in the processing tank 10, the opening portion of the processing tank 10 is closed by the lid 4.

The processing tank 10 includes a first tank 11 placed at a lowermost tier, and a second tank 12 that communicates with the first tank. The first tank 11 is disposed below a lowest part of the second tank 12, and has a predetermined first capacity. The capacity of the first tank is smaller than a capacity of the second tank 12.

An inner space of the first tank 11 and an inner space of the second tank 12 only need to be in communication with each other. For example, a form in which the first tank 11 and the second tank 12 are connected by, e.g., a conduit-like member and the cross-sectional area of the opening is narrowed at the connection portion may be employed. Also, for example, a net-like member may be disposed between the first tank 11 and the second tank 12.

In the present embodiment, as an example, the first tank 11 is a recessed portion provided in a lowest part of a bottom face of the second tank 12 so as to be recessed downward. Therefore, as illustrated in FIG. 1, as the processing tank 10 is viewed from above, the first tank 11 that opens to the bottom face of the second tank 12 can be seen. More specifically, the first tank 11 opens in the vicinity of an outer edge portion of the bottom face of the second tank 12.

Also, in the present embodiment illustrated, as an example, the second tank 12 includes a stepped portion in which a part of the bottom face bulges upward. In the bottom face of the second tank 12, a lower part is referred to as a lower-step portion 12a and the part that bulges upward relative to the lower-step portion is referred to as an upper-step portion 12b.

Note that the stepped portion of the second tank 12 is formed so as to conform to an outer shape of an endoscope 100 in order to receive the endoscope 100 inside the second tank 12. Therefore, the second tank 12 may have a shape including no stepped portion.

In the processing tank 10, a restriction portion 7, a water level sensor 6, a drainage port 20, a circulation port 30, ejection portions 36, a water charging port 58, a cleaning liquid charging port 53 and a disinfecting liquid charging port 25 are disposed.

The restriction portion 7 restricts an endoscope 100 placed in the second tank 12 of the processing tank 10 from entering the first tank 11. A configuration of the restriction portion 7 is not specifically limited as long as the configuration is a configuration that restricts the endoscope 100 from entering the inside of the first tank 11.

For example, the restriction portion 7 may be a net-like member that is provided in the vicinity of a boundary between the first tank 11 and the second tank 12 and has a mesh that prevents the endoscope 100 from penetrating therethrough. Also, for example, the restriction portion 7 may be a frame-like or basket-like member that holds the endoscope 100 in a predetermined position in the second tank 12.

In the present embodiment, as an example, the restriction portion 7 is a member having a columnar outer shape, the member being provided in the vicinity of the boundary between the first tank 11 and the second tank 12 so as to project upward relative to the bottom face of the second tank 12. More specifically, the restriction portion 7 is disposed at a part that is an outer edge portion of the opening of the first tank 11 and is close to the endoscope 100 placed in the second tank 12 relative to a center portion of the opening of the first tank 11. In other words, the restriction portion 7 is positioned between the endoscope 100 placed on in the second tank 12 and the opening of the first tank 11 and thereby prevents the endoscope 100 from moving into the first tank 11 and an area that is above the opening of the first tank 11.

Therefore, in the present embodiment, as illustrated in FIG. 2, when the endoscope 100 is placed in the processing tank 10, the first tank 11 is not covered by the endoscope 100 as the processing tank 10 is viewed from above.

Also, as an example, the restriction portion 7 in the present embodiment includes the later-described water level sensor 6. In other words, the restriction portion 7 in the present embodiment doubles as an exterior member of the water level sensor 6, and thus the restriction portion 7 and the water level sensor 6 are integrated with each other. Note that the restriction portion 7 and the water level sensor 6 may be different members provided at different sites.

The water level sensor 6 is a part that detects a level of a liquid surface of a liquid existing in the processing tank 10. Although in the following description, a level of a liquid surface in the processing tank 10 is referred to as a water level, the liquid providing the "water level" is not limited to "water", and may be another liquid such as a cleaning liquid or a disinfecting liquid.

More specifically, for each of three levels determined in advance in the processing tank 10, i.e., a first water level L1, a second water level L2 and a third water level L3, the water level sensor 6 detects whether or not the relevant level is submerged in water. The water level sensor 6 is electrically connected to the control section 2.

The first water level L1 is a level that is equal to that of the lowest part of the bottom face of the second tank 12 or a level below the lowest part of the bottom face in the processing tank 10. In the present embodiment, as an example, the first water level L1 is a level that is equal to that of the lowest part of the bottom face of the second tank 12 and is located at a position that is the boundary between the first tank 11 and the second tank 12. In other words, when a water level in the processing tank 10 is equal to the first water level, the first tank 11 is filled with the liquid and the liquid does not exist in the second tank 12. It is assumed that a capacity of a part up to the first water level L1 of the processing tank 10 is a first capacity V1. In the present embodiment, a capacity of the first tank corresponds to the first capacity V1.

Figure 4:
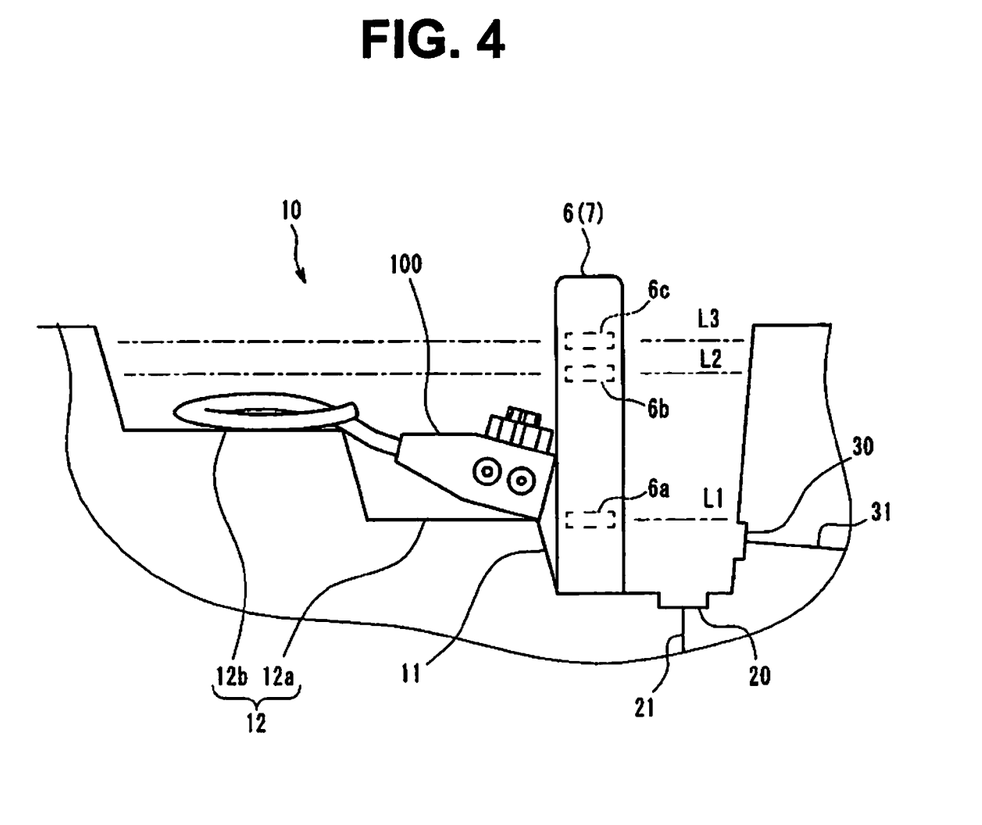
FIG. 4 is a diagram illustrating configurations of the processing tank and a water level sensor in the endoscope reprocessor according to the first embodiment.

The second water level L2 is a level that is above the lowest part of the bottom face of the second tank 12, and, in the present embodiment, is above a bottom face of the upper-step portion 12b of the second tank 12. As illustrated in FIG. 4, the second water level L2 is above a highest part of the endoscope 100 placed in the processing tank 10. In other words, if a liquid is stored up to the second water level L2 in the processing tank 10, the entire endoscope 100 is submerged in the liquid. It is assumed that a capacity up to the second water level L2 of the processing tank 10 is a second capacity V2. Also, the third water level L3 is a level that is above the second water level L2.

A configuration of the water level sensor 6 is not specifically limited, and the water level sensor 6 may be formed, for example, so as to be capable of successively measuring water level change in an entire area from a lowest water level to a highest water level in the processing tank 10, or may also be formed, for example, so as to, for each of only the three parts, i.e., the first water level L1, the second water level L2 and the third water level L3, determine whether a current water level is above or below the relevant level.

In the present embodiment, as an example, as illustrated in FIG. 4, the water level sensor 6 includes a first water level detection section 6a, a second water level detection section 6b and a third water level detection section 6c. The first water level detection section 6a, the second water level detection section 6b and the third water level detection section 6c detect whether or not the first water level L1, the second water level L2 and the third water level L3 are submerged in a liquid existing in the processing tank 10, respectively.

Each of the first water level detection section 6a, the second water level detection section 6b and the third water level detection section 6c has, for example, a configuration of what is called a float-type water meter including a switch that is opened/closed according to upward/downward movement of a float floating on a liquid.

Here, each of the first water level detection section 6a, the second water level detection section 6b and the third water level detection section 6c may have, e.g., a configuration of what is called an electrode-type water meter that detects, based on existence or non-existence of electric connection between each of electrodes arranged at the first water level L1, the second water level L2 and the third water level L3 and an electrode arranged below the first water level L1 in the processing tank 10, whether or not the relevant electrode is submerged in a liquid.

The drainage port 20 is an opening portion provided at a lowest site in the processing tank 10. In other words, the drainage port 20 is provided in a bottom face of the first tank 11. The drainage port 20 is connected to one end of a discharge conduit 21.

In the discharge conduit 21, a valve 24 and a discharge pump 22 are provided. The valve 24 opens/closes the discharge conduit 21 according to an instruction from the control section 2. The discharge pump 22 operates according to an instruction from the control section 2, and transfers a fluid in the discharge conduit 21 from the drainage port 20 to the other end 21b by means of the operation.

In other words, as a result of the valve 24 being brought into an opened state and operation of the discharge pump 22 being started, a liquid existing in the processing tank 10 is discharged from the other end 21b of the discharge conduit 21 via the drainage port 20 and the discharge conduit 21. Note that the other end 21b of the discharge conduit 21 is connected to a drainage facility for receiving drained liquid, via, e.g., a hose. The drainage facility is provided in a facility or the like in which the endoscope reprocessor 1 is installed.

Also, a collection conduit 29 is connected to the valve 24. In addition to switching between an opened state and a closed state of the discharge conduit 21, the valve 24 can make switch to a state in which the side of the discharge conduit 21 connected to the drainage port 20 and the collection conduit 29 are in communication with each other. The collection conduit 29 brings the valve 24 and a disinfecting liquid tank 28 that stores a disinfecting liquid into communication with each other. If the valve 24 is in a state in which the valve 24 provides communication between the side of the discharge conduit 21 connected to the drainage port 20 and the collection conduit 29, the liquid existing in the processing tank 10 is introduced into the disinfecting liquid tank 28.

The circulation port 30 is an opening portion provided at a level that is below the first water level L1 in the first tank 11 and is a predetermined distance above the bottom face of the first tank 11. More specifically, in a state in which the liquid is stored up to the first water level L1 in the processing tank 10, the circulation port 30 is provided at a level at which the entire circulation port 30 is submerged under the liquid surface. One end of a circulation conduit 31 is connected to the circulation port 30.

The other end of the circulation conduit 31 is connected to the ejection portions 36, which communicate with the circulation port 30 via the circulation conduit 31. The ejection portions 36 are disposed above the first water level L1. As illustrated in FIG. 2, connection tubes 110 are connectable to the ejection portions 36. The connection tubes 110 are connectable to respective fitting portions 101 of conduits included in the endoscope 100. As a result of the connection tubes 110 being connected to the ejection portions 36 and the fitting portions 101, the circulation conduit 31 and the conduits of the endoscope 100 come into communication with each other.

In the present embodiment, as an example, a plurality of ejection portions 36 are provided, and the plurality of ejection portions 36 are individually opened/closed by a channel valve 34. The channel valve 34 operates based on an instruction from the control section 2.

In the circulation conduit 31, a circulation pump 32 is disposed. The circulation pump 32 operates according to an instruction from the control section 2, and transfers a fluid in the circulation conduit 31 from the circulation port 30 toward the ejection portions 36 by means of the operation.

As a result of operation of the circulation pump 32 being started in a state in which a liquid is stored up to the first water level L1 in the processing tank 10, the liquid existing in the processing tank 10 is ejected from the ejection portions 36 via the circulation port 30 and the circulation conduit 31. Where the ejection portions 36 are connected to the conduits of the endoscope 100, the liquid ejected from the ejection portions 36 returns to the inside of the processing tank 10 via the conduits of the endoscope 100. In other words, as a result of the operation of the circulation pump 32, the liquid in the processing tank 10 can be circulated.

An air feeding conduit 37 and an alcohol conduit 41 are connected to a section of the circulation conduit 31 between the circulation pump 32 and the channel valve 34.

In the air feeding conduit 37, an air feeding pump 38 is disposed. The air feeding pump 38 operates according to an instruction from the control section 2 and feeds air into the circulation conduit 31 by means of the operation. In other words, as a result of operation of the air feeding pump 38 being started, air is ejected from the ejection portions 36. A check valve 39 is provided in a section of the air feeding conduit 37 between a portion of connection with the circulation conduit 31 and the air feeding pump 38. The check valve 39 prevents fluid in the circulation conduit 31 from flowing into the air feeding conduit 37.

The alcohol conduit 41 brings the circulation conduit 31 and an alcohol tank 40 that stores alcohol into communication with each other. In the alcohol conduit 41, an alcohol pump 42 is disposed. The alcohol pump 42 operates according to an instruction from the control section 2 and feeds alcohol in the alcohol tank 40 into the circulation conduit 31 by means of the operation. In other words, as a result of operation of the alcohol pump 42, alcohol is ejected from the ejection portions 36. A check valve 43 is provided in a section of the alcohol conduit 41 between a portion of connection with the circulation conduit 31 and the alcohol pump 42. The check valve 43 prevents fluid in the circulation conduit 31 from entering the alcohol conduit 41.

The water charging port 58 is a nozzle disposed above the processing tank 10. The water charging port 58 is connected to a water tap connection portion 55 via a water conduit 56. In the water conduit 56, a water supply valve 57 is disposed. The water supply valve 57 opens/closes the water conduit 56 according to an instruction from the control section 2. A water supply portion 60 that ejects water, for example, a water faucet, the water supply portion 60 being provided outside the endoscope reprocessor 1, is connected to the water tap connection portion 55. As a result of the water supply valve 57 being brought into an opened state, water ejected from the water supply portion 60 is introduced into the processing tank 10 via the water conduit 56 and the water charging port 58.

The cleaning liquid charging port 53 is a nozzle disposed above the processing tank 10. The cleaning liquid charging port 53 is connected to a cleaning liquid tank 50 that stores a cleaning liquid via a cleaning liquid conduit 51. In the cleaning liquid conduit 51, a cleaning liquid pump 52 is disposed. The cleaning liquid pump 52 operates according to an instruction from the control section 2 and feeds the cleaning liquid in the cleaning liquid tank 50 into the cleaning liquid charging port 53 by means of the operation. In other words, as a result of operation of the cleaning liquid pump 52, the cleaning liquid is ejected from the cleaning liquid charging port 53 and introduced into the processing tank 10.

In the present embodiment, as an example, as illustrated in FIG. 2, the cleaning liquid charging port 53 is disposed above the opening of the first tank 11, and the cleaning liquid ejected from the cleaning liquid charging port 53 drops down into the opening of the first tank 11. As described above, the restriction portion 7 prevents the endoscope 100 from being positioned above the opening of the first tank 11. Therefore, the cleaning liquid charging port 53 can be regarded as being disposed at a position that prevents the cleaning liquid ejected from the cleaning liquid charging port 53 from dropping down onto the endoscope 100 placed in the processing tank 10.

The disinfecting liquid charging port 25 is a nozzle disposed above the processing tank 10. The disinfecting liquid charging port 25 is connected to the disinfecting liquid tank 28 that stores a disinfecting liquid, via a disinfecting liquid conduit 26. In the disinfecting liquid conduit 26, a disinfecting liquid pump 27 is disposed. The disinfecting liquid pump 27 operates according to an instruction from the control section 2 and feeds the disinfecting liquid in the disinfecting liquid tank 28 into the disinfecting liquid charging port 25 by means of the operation. In other ward, as a result of operation of the disinfecting liquid pump 27, the disinfecting liquid is ejected from the disinfecting liquid charging port 25 and introduced into the processing tank 10. Also, as described above, upon switching of the valve 24 being made so as to provide communication between the drainage port 20 and the collection conduit 29 in a state in which the disinfecting liquid exists in the processing tank 10, the disinfecting liquid existing in the processing tank 10 returns into the disinfecting liquid tank 28.

Next, operation of the endoscope reprocessor 1 will be described. The following operation is performed by the control section 2 based on the predetermined program.

Figure 5:
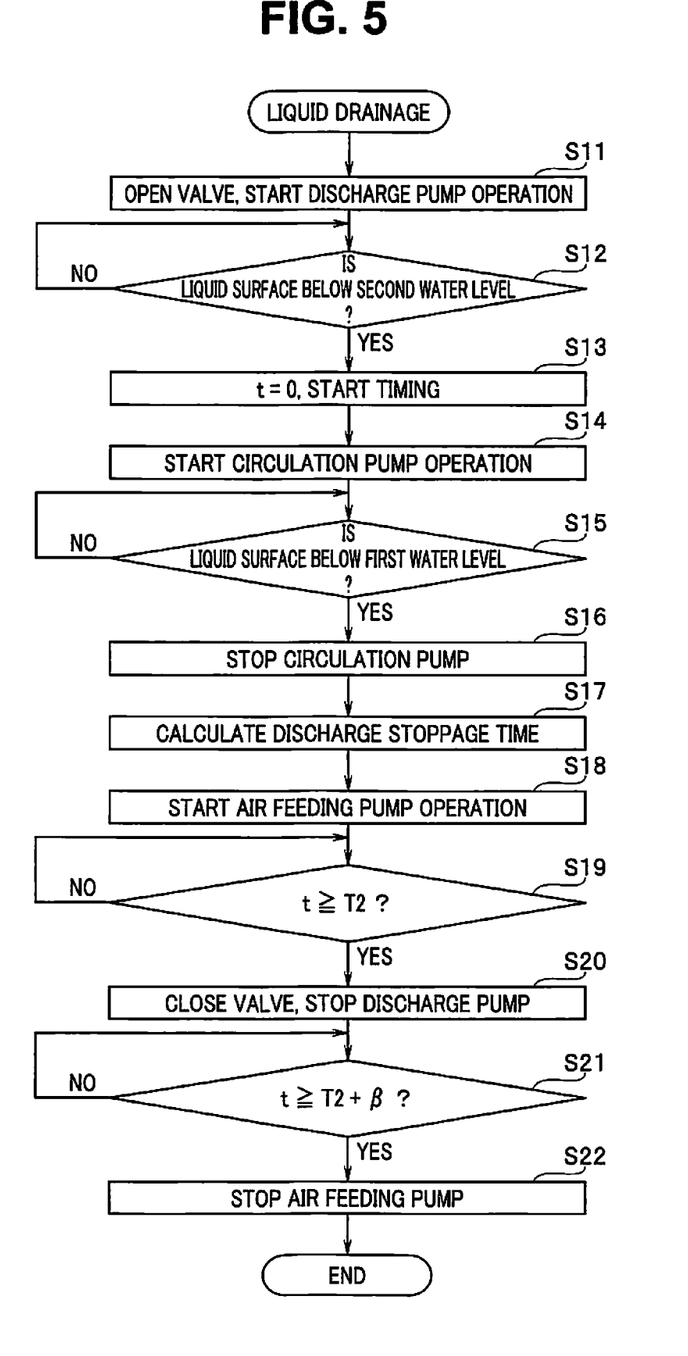
FIG. 5 is a flowchart of a drainage process in the endoscope reprocessor according to the first embodiment.

First, a drainage process of discharging liquid existing in the processing tank 10 in the endoscope reprocessor 1 will be described. FIG. 5 is a flowchart of a drainage process in the endoscope reprocessor 1.

The drainage process is performed, for example, during rinsing processing or cleaning processing in which an endoscope 100 is placed in the processing tank 10 and the endoscope 100 is immersed in water or a cleaning liquid, which is liquid.

Figure 6:
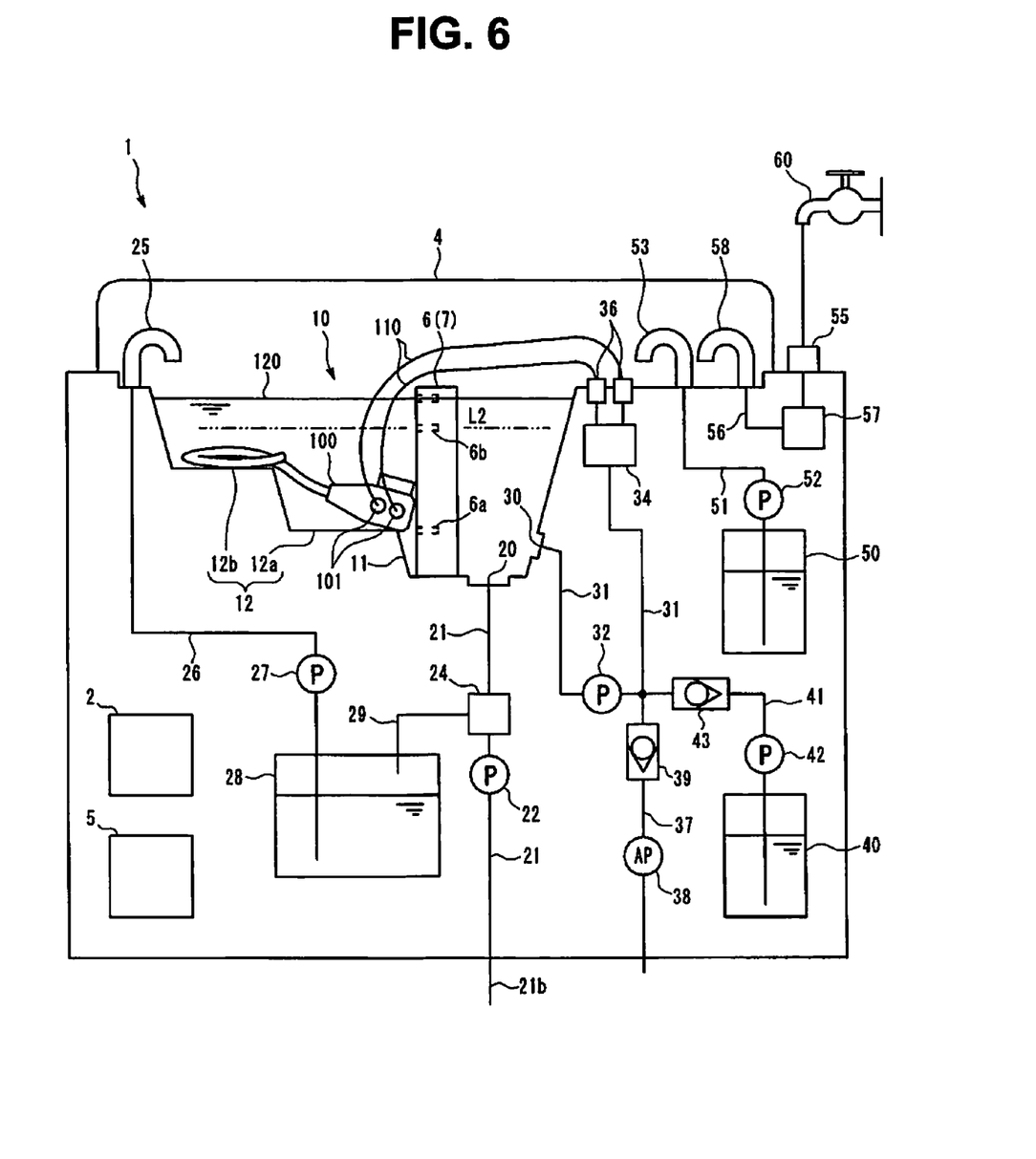
FIG. 6 is a diagram illustrating a state of the endoscope reprocessor according to the first embodiment at a point of time of a start of drainage processing.

At the start of the drainage process, as illustrated in FIG. 6, the endoscope 100 is placed in the processing tank 10. Fitting portions 101 of the endoscope 100 are connected to the ejection portions 36 via connection tubes 110.

Also, at the start of the drainage process, a liquid 120, which is water or a cleaning liquid, is stored in the processing tank 10. In other words, the valve 24 is in a closed state, and the discharge pump 22 and the circulation pump 32 are stopped. A liquid surface of the liquid 120 at the start of the drainage process is above the second water level L2.

In the drainage process, first, in step S11, the valve 24 is brought into an opened state, and operation of the discharge pump 22 is started. As a result of the execution of step S11, the liquid 120 in the processing tank 10 starts being discharged to the outside of the endoscope reprocessor 1 via the drainage port 20 and the discharge conduit 21. Therefore, as a result of the execution of step S11, the water level in the processing tank 10 starts lowering.

In step S12, lowering of the liquid surface to below the second water level L2 is waited for. Determination in step S12 is made based on an output signal from the second water level detection section 6b of the water level sensor 6. Then, after detection of lowering of the liquid surface to below the second water level L2, the process moves to step S13.

In step S13, timing by means of the timing section included in the control section 2 is started. In the present embodiment, as an example, timing by means of a timer t is started with a point of time of execution of step S13 as zero seconds. In other words, a value of the timer t indicates a period of time passed from a point of time of detection of lowering of the liquid surface to below the second water level L2.

Next, in step S14, operation of the circulation pump 32 is started. As a result of the start of operation of the circulation pump 32, the liquid 120 in the processing tank 10 flows and circulates so as to return to the processing tank 10 through the circulation port 30, the circulation conduit 31, the connection tubes 110 and conduits of the endoscope 100.

In step S15, lowering of the liquid surface to below the first water level L1 is waited for. Determination in step S15 is made based on an output signal from the first water level detection section 6a of the water level sensor 6. Then, after detection of lowering of the liquid surface to below the first water level L1, the process moves to step S16 and the circulation pump 32 is stopped.

In other words, from steps S14 to S16, even in the middle of discharge of the liquid 120 in the processing tank 10, the liquid 120 is made to flow into the conduits of the endoscope 100 during a period in which the liquid surface is positioned between the first water level L1 and the second water level L2.

Here, if the liquid surface is equal to or above the first water level L1, the circulation port 30 is submerged under the liquid surface and no air flows into the circulation conduit 31, and thus no idling of the circulation pump 32, which reduces the lifetime of the circulation pump 32, occurs.

As described above, in the present embodiment, the inclusion of the water level sensor 6 that detects whether a water level is above or below the first water level L1 enables the liquid 120 to flow into the conduits of the endoscope 100 even during a period in which discharge of the liquid 120 from the inside of the processing tank 10 is waited for. Thus, a time period in which the liquid 120 flows inside the conduits of the endoscope 100 can further be increased. Since the inside of the conduits of the endoscope 100 is parts to which dirt easily adheres and thus, in cleaning processing and rinsing processing, it is preferable to increase a time period in which a cleaning liquid or water flows inside the conduits.

Next, in step S17, a discharge stoppage time T2 is calculated. The discharge stoppage time T2 is a target time at which the valve 24 is brought into a closed state and the discharge pump 22 is stopped.

In step S17, first, the value of the timer t at a point of time of execution of step S17 is stored as a time period T1. The time period T1 is a time period from the point of time of lowering of the liquid surface to below the second water level L2 to the point of time of lowering of the liquid surface to below the first water level L1. In other words, the time period T1 is a time period required for discharge of a volume V3 of the liquid 120 from the processing tank 10. The volume V3 is smaller than a difference between the second capacity V2 and the first capacity V1 by the amount of the volume of the endoscope 100, etc., placed in the processing tank 10.

Then, in step S17, the discharge stoppage time T2 is calculated based on the value of the time period T1 consumed for lowering of the liquid surface from the second water level L2 to the first water level L1. In the present embodiment, as an example, the discharge stoppage time T2 is calculated according to the following equation.

$$T2 = T1 \cdot (1 + V1/V2) + \alpha$$

Here, as described above, V1 is a capacity up to the first water level L1 of the processing tank 10, and V2 is a capacity up to the second water level L2 of the processing tank 10. Also, α is a predetermined constant and a time allowance provided for absorbing the impact of variation of the volume V3.

Next, in step S18, operation of the air feeding pump 38 is started. At a point of time of execution of step S18, the liquid surface is below the first water level L1 and inside the first tank 11, the endoscope 100 placed in the second tank 12 is positioned above the liquid surface. Therefore, a process of starting the operation of the air feeding pump 38 to feed air into the conduits of the endoscope 100 and thereby removing the liquid 120 in the conduit can be started during a period in which discharge of the liquid 120 from the inside of the processing tank 10 is waited for. In other words, in the present embodiment, a period in which a drainage process of discharging the liquid 120 from the processing tank 10 and a period in which a water removal process of blowing away the liquid 120 in the conduits of the endoscope 100 can be overlapped, enabling reduction in time period required for processing of the endoscope 100 using the liquid 120.

Then, in step S19, the value of the timer t reaching the discharge stoppage time T2 is waited for. Upon the value of the timer t reaching the discharge stoppage time T2, the process moves to step S20, and the valve 24 is brought into a closed state and the discharge pump 22 is stopped.

Next, in step S21, the value of the timer t reaching a value of the discharge stoppage time T2 plus a predetermined time period β is waited for. In other words, in step S21, the valve 24 is brought into a closed state and the discharge pump 22 is stopped, and then a lapse of the time period β is waited for. Upon the value of the timer t reaching the value of the discharge stoppage time T2 plus the predetermined time period β, the process moves to step S22. In step S22, the air feeding pump 38 is stopped.

As described above, in the present embodiment, in the drainage process, at a point of time of the liquid surface in the processing tank 10 falling below the first water level L1, a discharge stoppage time T2, which is a timing for bring the valve 24 into a closed state and stopping the discharge pump 22, is determined.

Here, since the first water level L1 is a level of the boundary between the first tank 11 disposed below and the second tank 12 disposed above, when the liquid surface in the processing tank 10 is at the first water level L1, the liquid 120 exists only in the first tank 11. Then, in the present embodiment, as a result of the provision of the restriction portion 7, no part of the endoscope 100 exists in the first tank 11. Therefore, at a point of time of lowering of the liquid surface in the processing tank 10 to the first water level L1 in the drainage process, the volume of the liquid 120 existing in the processing tank 10 corresponds to the first capacity V1, which is the capacity up to the first water level L1 of the processing tank 10, and is constant irrespective of variation in volume of the endoscope 100.

Thus, in the present embodiment, a correct time period required to discharge the entire liquid 120 from the processing tank 10 can be calculated with no influence of volume variation depending on the endoscope 100, and a conventionally-needed wait time period is reduced, enabling reduction in time period required for a drainage process.

Also, in the present embodiment, the discharge stoppage time T2 is calculated from the time period T1 required for lowering of the liquid surface from the second water level L2 to the first water level L1. Then, as the time period T1 is shorter, a time period from a point of time of the liquid surface falling below the first water level L1 until the valve 24 is brought into a closed state and the discharge pump 22 is stopped becomes shorter.

In the endoscope reprocessor 1, a flow rate of the liquid 120 discharged from the discharge conduit 21 in the drainage process varies depending on, for example, the shape or the installation manner of the hose connected to the other end 21b of the discharge conduit 21. Variation in flow rate of the liquid 120 discharged from the discharge conduit 21 can be indicated as increase/decrease in length of the time period T1. For example, as the flow rate of the liquid 120 discharged from the discharge conduit 21 is larger, the time period T1 is shorter.

In the present embodiment, as the time period T1 is shorter, the discharge stoppage time T2 is set to be shorter, and thus, a time period required for the drainage process can be reduced. In other words, in the present embodiment, the discharge stoppage time T2 is calculated in consideration of variation in flow rate of the liquid 120 discharged from the discharge conduit 21, enabling reduction in wait time period required when flow rate variation is not taken into consideration.

Figure 7:
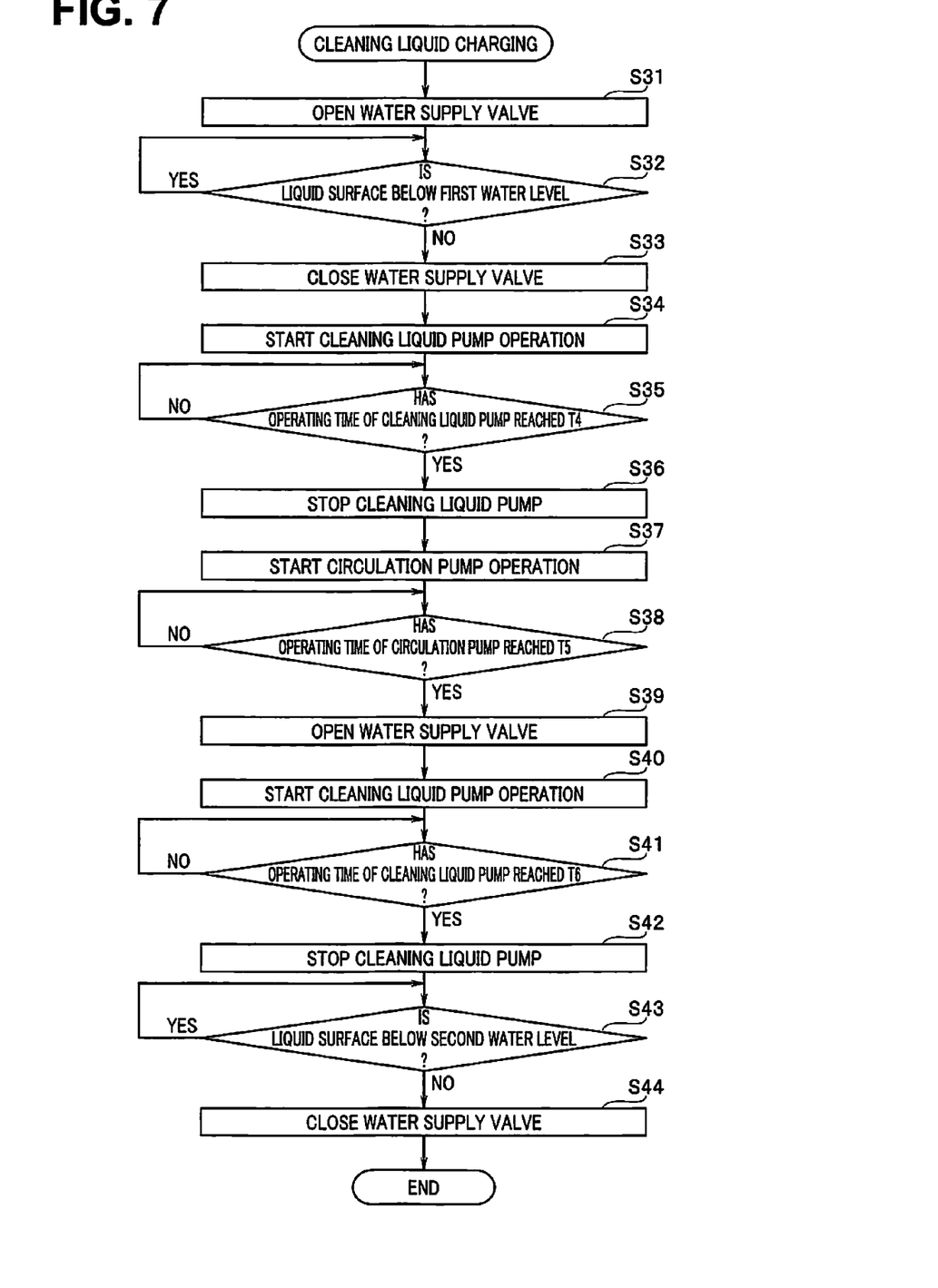
FIG. 7 is a flowchart of a cleaning liquid charging process in the endoscope reprocessor according to the first embodiment.

Next, a cleaning liquid charging process of charging a cleaning liquid into the processing tank 10 in the endoscope reprocessor 1 will be described. FIG. 7 is a flowchart of a cleaning liquid charging process in the endoscope reprocessor 1.

The cleaning liquid charging process is performed when cleaning processing using a cleaning liquid, which is liquid, is performed on an endoscope 100 placed in the processing tank 10. In cleaning processing in the present embodiment, a diluted cleaning liquid obtained by diluting the cleaning liquid stored in the cleaning liquid tank 50 with water at a predetermined ratio is used.

At the start of the cleaning liquid charging process, an endoscope 100 is placed in the processing tank 10, the valve 24 is in a closed state and the pumps such the cleaning liquid pump 52 and the circulation pump 32 is stopped. Also, at the start of the cleaning liquid charging process, the liquid in the processing tank 10 has completely been discharged.

In the cleaning liquid charging process, first, in step S31, the water supply valve 57 is brought into an opened state. As a result of the water supply valve 57 being brought into an opened state, introduction of water from the water charging port 58 into the processing tank 10 is started.

In step S32, rising of the liquid surface to the first water level L1 is waited for. Determination in step S32 is made based on an output signal from the first water level detection section 6a of the water level sensor 6. Then, after detection of rising of the liquid surface to the first water level L1, the process moves to step S33.

In step S33, the water supply valve 57 is brought into a closed state. At the point of time of execution of step S33, the predetermined volume V1 of water is stored in the processing tank 10. Also, at this time, the water is stored in the first tank 11.

Next, in step S34, operation of the cleaning liquid pump 52 is started. As a result of operation of the cleaning liquid pump 52 being started, the cleaning liquid stored in the cleaning liquid tank 50 is started to be introduced from the cleaning liquid charging port 53 into the processing tank 10.

Here, the cleaning liquid charging port 53 is positioned above the opening of the first tank 11, the cleaning liquid ejected from the cleaning liquid charging port 53 directly drops down into the opening of the first tank 11 and is mixed with the water stored in the first tank 11. In other words, in the present embodiment, a high concentration of cleaning liquid before dilution with water is prevented from coming into contact with the endoscope 100 placed in the processing tank 10. Thus, it is possible to prevent a high concentration of cleaning liquid having a high level of aggression toward, e.g., resins from coming into contact with the endoscope 100.

Next, in step S35, an operating time period of the cleaning liquid pump 52 reaching a predetermined time period T4 is waited for. Upon the operating time period of the cleaning liquid pump 52 reaching the predetermined time period T4, the process moves to step S36 and the cleaning liquid pump 52 is stopped.

As a result of making the cleaning liquid pump 52 operates for the predetermined time period T4, a predetermined volume of the cleaning liquid is introduced from the cleaning liquid tank 50 into the first tank 11 in the processing tank 10. Here, in steps S34 to S36, a volume of the cleaning liquid introduced into the first tank 11 in the processing tank 10 is determined so that a mixture ratio between the volume of the cleaning liquid and the predetermined volume V1 of water is a value suitable for subjecting the endoscope 100 to cleaning processing. In other words, after the execution of step S36, the diluted cleaning liquid resulting from dilution with water at the predetermined ratio, with the volume allowing the liquid surface to be positioned above the first water level L1, is stored in the processing tank 10. Also, after the execution of step S36, the circulation port 30 is submerged under the liquid surface.

Next, in step S37, operation of the circulation pump 32 is started. As a result of operation of the circulation pump 32 being started, the diluted mixture in the processing tank 10 flows and circulates so as to return to the processing tank 10 through the circulation port 30, the circulation conduit 31, connection tubes 110 and conduits of the endoscope 100. Here, the circulation port 30 is submerged under the liquid surface and no air flows into the circulation conduit 31, and thus no idling of the circulation pump 32, which reduce the lifetime of the circulation pump 32, occurs.

Then, in step S38, the operating time period of the circulation pump 32 reaching a predetermined time period 15 is waited for. Upon the operating time period of the circulation pump 32 reaching the predetermined time period T5, in step S39, the water supply valve 57 is brought into an opened state, and in step S40, operation of the cleaning liquid pump 52 is started.

Then, as indicated in steps S41 and S42, the cleaning liquid pump 52 is stopped after operation for a predetermined time period T6. Here, the predetermined time period T6 is shorter than a time period required for water introduced from the water charging port into the processing tank 10 to reach the second water level L2.

As a result of the execution of steps S41 and S42, a predetermined volume of the cleaning liquid is transferred from the cleaning liquid tank 50 into the processing tank 10. Here, a value of the cleaning liquid introduced into the processing tank 10 by the execution of steps S41 and S42 is set to be a value necessary for filling a volume from the first water level L1 to the second water level L2 with the diluted cleaning liquid with the predetermined ratio.

Next, in step S43, rising of the liquid surface to the second water level L2 is waited for. Determination in step S43 is made based on an output signal from the second water level detection section 6b of the water level sensor 6. Then, after detection of rising of the liquid surface to the second water level L2, the process moves to step S44.

In step S44, the water supply valve 57 is brought into a closed state. At the point of time of execution of step S44, a volume of the diluted cleaning liquid, the volume enabling the entire endoscope 100 to be immersed in the diluted cleaning liquid, is stored in the processing tank 10. In other words, at the point of time of execution of step S44, the entire endoscope 100 is submerged in the diluted cleaning liquid resulting from dilution at the predetermined ratio.

As described above, in the cleaning liquid charging process in the present embodiment, as indicated in steps S31 to S36, first, a predetermined volume of diluted cleaning liquid, the volume bringing the liquid surface to a level above the circulation port 30, is produced in the first tank 11, and as indicated in steps S37 and S38, introduction of the diluted cleaning liquid into the conduits of the endoscope 100 is started. Subsequently, as illustrated in steps S39 to S44, a volume of diluted cleaning liquid, the volume allowing the endoscope 100 to be submerged under the liquid surface, is produced.

As described above, in the cleaning liquid charging process in the present embodiment, during a period in which production of a volume of diluted cleaning liquid, the volume enabling the entire endoscope 100 to be immersed in the diluted cleaning liquid, is waited for, introduction of a diluted cleaning liquid resulting from dilution at the predetermined ratio into the conduits of the diluted endoscope 100 can be started, enabling increase in period of time of cleaning the inside of the conduits. The inside of the conduits of the endoscope 100 are parts to which dirt more easily adheres compared to, e.g., exterior members and for which a longer period of time is desirably consumed for cleaning processing. The present embodiment is favorable because cleaning of the inside of the conduits can be started during a waiting time period and thus a period of time of cleaning the inside of the conduits can be increased without increase in period of time necessary for cleaning processing of the endoscope 100.

Figure 8:
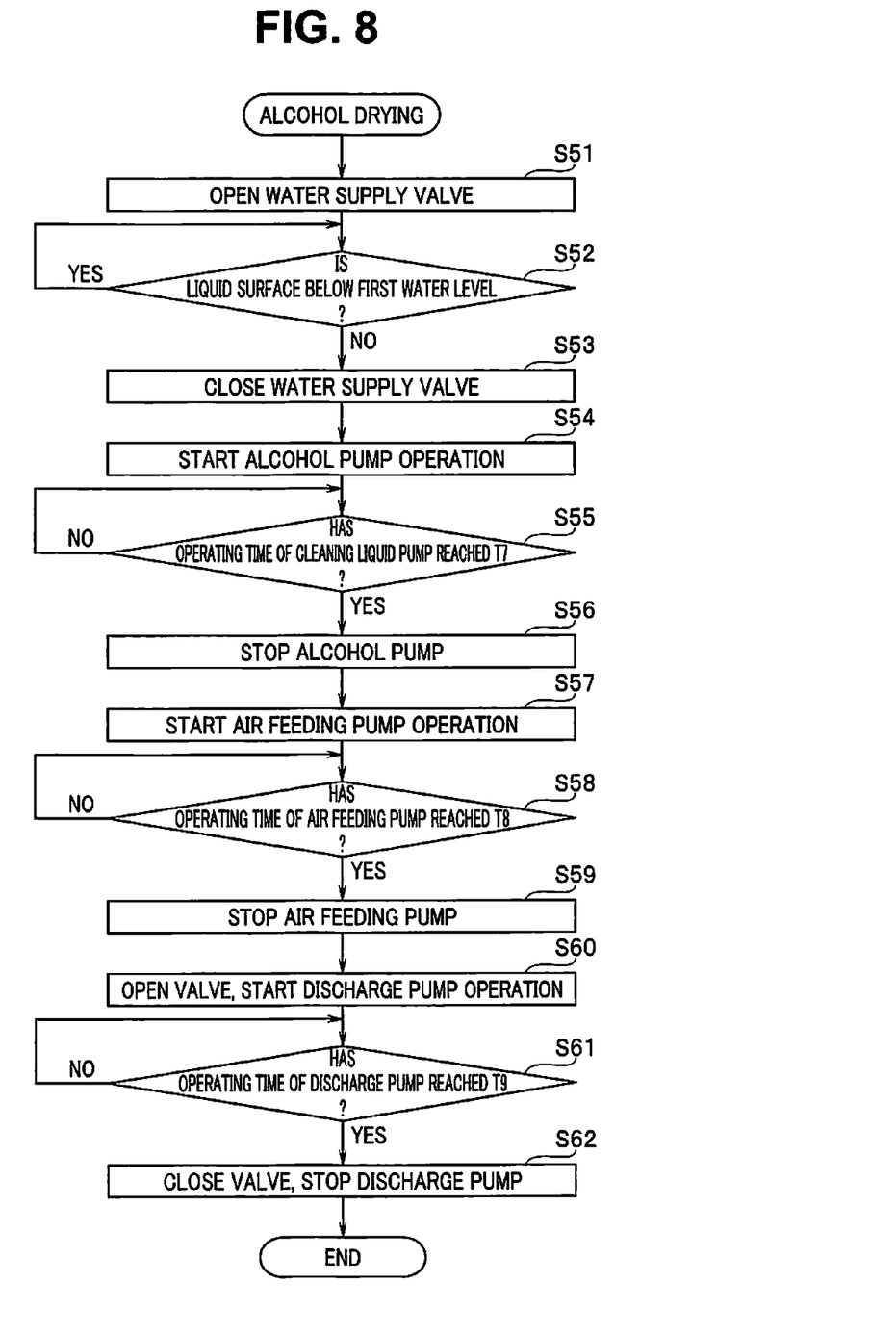
FIG. 8 is a flowchart of an alcohol drying process in the endoscope reprocessor according to the first embodiment.

Next, an alcohol drying process of introducing alcohol into conduits of an endoscope 100 to promote drying of the inside of the conduits in the endoscope reprocessor 1 will be described. FIG. 8 is a flowchart of an alcohol drying process in the endoscope reprocessor 1.

At the start of the alcohol drying process, an endoscope 100 is placed in the processing tank 10, the valve 24 is in a closed state, and the pumps such as the cleaning liquid pump 52 and the circulation pump 32 are stopped. Also, at the start of the alcohol drying process, the liquid in the processing tank 10 has completely been discharged.

In the alcohol drying process, first, in step S51, the water supply valve 57 is brought into an opened state. As a result of the water supply valve 57 being brought into an opened state, introduction of water from the water charging port 58 into the processing tank 10 is started.

In step S52, rising of the liquid surface to the first water level L1 is waited for. Determination in step S52 is made based on an output signal from the first water level detection section 6a of the water level sensor 6. Then, after detection of rising of the liquid surface to the first water level L1, the process moves to step S53.

In step S53, the water supply valve 57 is brought into a closed state. At the point of time of execution of step S53, the predetermined volume V1 of water is stored in the processing tank 10.

Next, in step S54, operation of the alcohol pump 42 is started. As a result of operation of the alcohol pump 42 being started, alcohol is started to be introduced into the alcohol conduit 41 and the circulation conduit 31.

Next, in step S55, an operating time period of the alcohol pump 42 reaching a predetermined time period T7 is waited for. Upon the operating time period of the alcohol pump 42 reaching the predetermined time period T7, the process moves to step S56 and the alcohol pump 42 is stopped.

Next, in step S57, operation of the air feeding pump 38 is started. As a result of operation of the air feeding pump 38 being started, the alcohol in the circulation conduit 31 is introduced together with air into conduits of the endoscope 100 via connection tubes 110. The alcohol is introduced into the processing tank 10 via the conduits of the endoscope 100 and is mixed and diluted with water stored in advance in the processing tank 10. As a result of the alcohol being diluted with water in the processing tank 10, increase in alcohol concentration in air in the processing tank 10 is prevented.

Next, in step S58, an operating time period of the air feeding pump 38 reaching a predetermined time period T8 is waited for. Upon the operating time period of the air feeding pump 38 reaching the predetermined time period T8, the process moves to step S59 and the air feeding pump 38 is stopped. As a result of the execution of the steps up to step S58, alcohol and air are fed into the conduits of the endoscope 100 and removal of moisture in the conduits is completed.

Next, in step S59, the valve 24 is brought into an opened state, and operation of the discharge pump 22 is started. As a result of the execution of step S59, the water and the alcohol in the processing tank 10 are started to be discharged to the outside of the endoscope reprocessor 1 via the drainage port 20 and the discharge conduit 21. Then, in step S61, an operating time period of the discharge pump 22 reaching a predetermined time period T9 is waited for. Upon the operating time period of the discharge pump 22 reaching the predetermined time period T9, the process moves to step S62, and the valve 24 is brought into a closed state and the discharge pump 22 is stopped.

As described above, in the present embodiment, at the time of an alcohol drying process being performed, measurement of an amount of water for dilution of alcohol is performed using the first water level detection section 6a of the water level sensor 6, enabling dilution of alcohol at a correct ratio.

Second Embodiment

Figure 9:
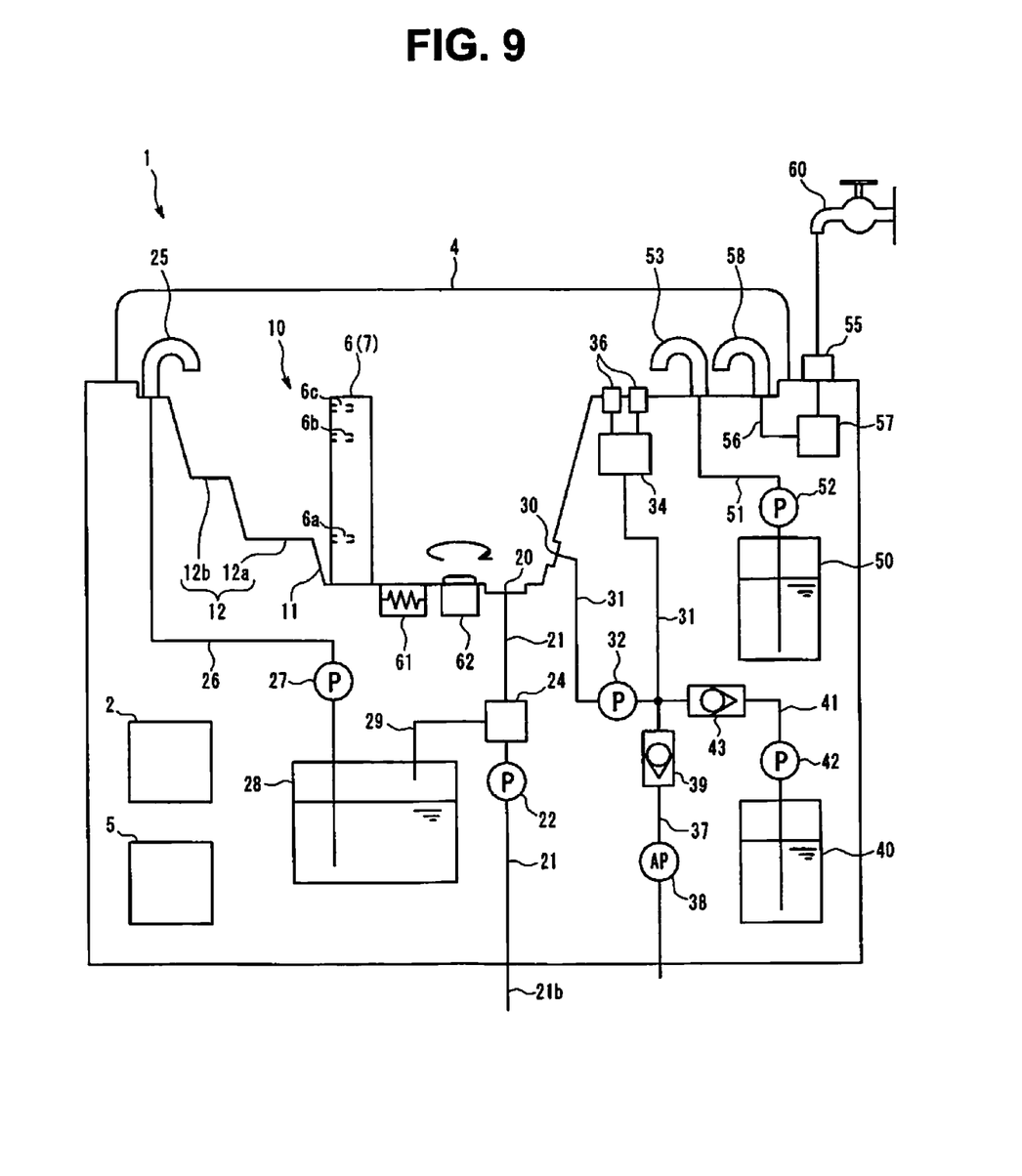
FIG. 9 is a diagram of a configuration of an endoscope reprocessor according to a second embodiment.

Next, a second embodiment of the present invention will be described. In the following, only differences from the first embodiment will be described, and components that are similar to those of the first embodiment will be described with reference numerals that are the same as those of the first embodiment, and description thereof will arbitrarily be omitted. As illustrated in FIG. 9, an endoscope reprocessor 1 according to the present embodiment is different from that of the first embodiment in inclusion of a heater 61 and a stirring apparatus 62.

The heater 61 is an apparatus that heats a liquid, for example, a disinfecting liquid stored in a processing tank 10 to a predetermined temperature. The stirring apparatus 62 is an apparatus that stirs the liquid in the processing tank 10. The liquid is heated by the heater 61 while the liquid is stirred by means of operation of the stirring apparatus 62, enabling the entire liquid in the processing tank 10 to be heated to the predetermined temperature without unevenness.

The stirring apparatus 62 is disposed in a first tank 11. A form of the stirring apparatus 62 is not specifically limited as long as the form causes the liquid stored in the processing tank 10 flow. In the present embodiment, as an example, a form of what is called a magnetic stirrer that rotates a stirring bar arranged in the processing tank 10 using an magnetic force by means of a drive apparatus arranged outside the processing tank 10 is employed.

In the present embodiment, disposition of a restriction portion 7 in the processing tank 10 prevents an endoscope 100 from entering the inside of the first tank 11. Therefore, disposition of the stirring apparatus 62 having a movable portion in the first tank 11 enables prevention of contact between the stirring apparatus 62 and the endoscope 100.

The rest of the configuration and operation of the endoscope reprocessor 1 according to the present embodiment is similar to that of the first embodiment. Therefore, the endoscope reprocessor 1 according to the present embodiment also enables provision of effects that are similar to those of the first embodiment.

Note that the present invention is not limited to the above-described embodiments and the embodiments can be arbitrarily altered without departing the spirit and idea of the invention that can be read from the claims and the entire description, and an endoscope reprocessor that involves such alteration also falls within the technical scope of the present invention.

What is claimed is:

1. An endoscope reprocessor comprising:
    a processing tank including a first tank that has a predetermined capacity and is arranged at a lowermost tier, and a second tank that communicates with the first tank, the processing tank allowing an endoscope to be placed in the processing tank;
    a drainage port arranged in the first tank;
    a valve that opens and closes the drainage port;
    a restriction portion that restricts the endoscope from entering the first tank;
    a first water level detection section that detects whether or not a first water level set to be a water level that is equal to or below a boundary between the first tank and the second tank is submerged in water;
    a second water level detection section that detects whether or not a second water level set to be above the endoscope placed in the second tank is submerged in water;
    a circulation port that opens at a level that is below the first water level and is a predetermined distance above a bottom face of the first tank in the processing tank;
    a circulation conduit including one end connected to the circulation port and another end that opens at a position that is above the first water level in the processing tank;
    a circulation pump that transfers a fluid in the circulation conduit from the one end toward the other end; and
    a controller configured to:
       measure a period of time passed from a point of time of detecting lowering of a liquid surface of a liquid in the processing tank to below the second water level to a point of time of detecting lowering of the liquid surface to below the first water level in a drainage process of bringing the valve into an opened state to discharge the liquid in the processing tank from the drainage port; and
       calculate a period of time from a point of time of lowering of the liquid surface to below the first water level to a point of time of bringing the valve into a closed state in the drainage process.

2. The endoscope reprocessor according to claim 1, wherein:
    the first tank opens in a bottom face of the second tank; and
    the first water level detection section is integrated with the restriction portion.

3. The endoscope reprocessor according to claim 1, wherein
    in the drainage process, the controller is further configured to make the circulation pump operate during a period in which the first water level detection section detects that a liquid surface of the liquid is above the first water level.

4. The endoscope reprocessor according to claim 3, comprising an air feeding pump that feeds air into a conduit included in the endoscope,
    wherein in the drainage process, after detection of lowering of the liquid surface of the liquid to below the first water level by the first water level detection section, the control section starts operation of the air feeding pump to start feeding of air into the conduit.

5. The endoscope reprocessor according to claim 1, further comprising:
    a cleaning liquid charging port arranged above an opening of the first tank; and
    a water supply valve that supplies water into the processing tank,
    wherein, in a cleaning liquid charging process of charging a cleaning liquid into the processing tank in an empty state from the cleaning liquid charging port, the controller is configured to:
       bring the water supply valve into an opened state to start supplying water into the processing tank, and after the first water level detection section detects rising of the liquid surface to above the first water level,
       charge a predetermined volume of the cleaning liquid from the cleaning liquid charging port into the processing tank, and
       after the second water level detection section detects rising of the liquid surface to above the second water level, bring the water supply valve into a closed state.

6. The endoscope reprocessor according to claim 1, further comprising:
    an air feeding pump that feeds air into a conduit included in the endoscope;
    an alcohol pump that feeds alcohol into the conduit; and
    a water supply valve that supplies water into the processing tank,
    wherein, in an alcohol drying process of introducing alcohol into the conduit to promote drying of an inside of the conduit, the controller is configured to:
       bring the water supply valve into an opened state to start supplying water into the processing tank,
       after the first water level detection section detects rising of the liquid surface to above the first water level, bring the water supply valve into a closed state, and thereafter drive the alcohol pump and the air feeding pump to introduce the alcohol into the conduit.

* * * * *